US008013601B2

(12) United States Patent
Cheng et al.

(10) Patent No.: US 8,013,601 B2
(45) Date of Patent: Sep. 6, 2011

(54) METHODS FOR DETERMINING IN SITU THE VISCOSITY OF HEAVY OIL USING NUCLEAR MAGNETIC RESONANCE RELAXATION TIME MEASUREMENTS

(75) Inventors: Yuesheng Cheng, Edmonton (CA); Abdel M. Kharrat, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 293 days.

(21) Appl. No.: 12/536,133

(22) Filed: Aug. 5, 2009

(65) Prior Publication Data

US 2010/0039109 A1    Feb. 18, 2010

(30) Foreign Application Priority Data

Aug. 15, 2008   (CA) ..................................... 2638697

(51) Int. Cl.
*G01V 3/00* (2006.01)
(52) U.S. Cl. ....................................................... 324/303
(58) Field of Classification Search .................. 324/300, 324/303; 73/54.01; 250/269.1
See application file for complete search history.

(56) References Cited

U.S. PATENT DOCUMENTS

| | | | |
|---|---|---|---|
| 4,747,958 A | 5/1988 | Eberhardt | |
| 7,511,487 B2 * | 3/2009 | Badry et al. | 324/303 |
| 7,511,488 B2 * | 3/2009 | Romero et al. | 324/303 |
| 7,965,078 B2 * | 6/2011 | Cheng et al. | 324/303 |
| 2008/0272773 A1 * | 11/2008 | Romero et al. | 324/300 |
| 2010/0033176 A1 * | 2/2010 | Cheng et al. | 324/303 |

OTHER PUBLICATIONS

James A. Zega, et al, Spin-Lattice Relaxation and Viscosity in Mixtures of n-Hexane and n-Hexadecane, Department of Chemical Engineering, Rice University, P.O. Box 1892, Houston, Texas 77251, 1990, p. 909-912.

The Log Analyst, A Journal of Formation Evaluation and Reservoir Description, Nov.-Dec. 1996, vol. 37, No. 6 p. 1-80.
Q. Zhang, et al, Some Exceptions to Default NMR Rock and Fluid Properties, SPWLA 39th Annual Logging Symposium, May 26-29, 1998, p. 1-14.
G.A. Latorraca, et al, Heavy Oil Viscoity Determination Using NMR Logs, SPWLA 40th Annual Logging Symposium, May 30-Jun. 3, 1999, p. 1-11.
J. Bryan et al, Oil-Viscosity Predictions from Low-Field NMR Measurements, SPE Reservoir Evaluation & Engineering, Feb. 11, 2005, pp. 44-52.
B. Nicot et al, A New Methodology for Better Viscosity Prediction Using NMR Relaxation, SPWLA 47th Annual Logging Symposium, Jun. 4-7, 2006, p. 1-12.
Malcolm L. Williams et al, The Temperature Dependence of Relaxation Mechanisms in Amorphous Polymers and Other Glass-forming Liquids.

* cited by examiner

*Primary Examiner* — Brij Shrivastav
(74) *Attorney, Agent, or Firm* — Jay P. Serollini; Wayne I. Kanak

(57) ABSTRACT

The viscosity $\eta$ (in centipoise) of a heavy oil sample is determined according to an equation of the form ln $$\frac{\eta}{\eta_g} = \frac{-C1 * (T - c'246)}{c''47.10 + (T - c'246)},$$

where T is the temperature of the heavy oil, $T_{2LM}$ is the logarithmic mean of the $T_2$ distribution of the sample obtainable from nuclear magnetic resonance (NMR) measurements, $c'=1.0\pm0.05$, $c''=1.0\pm0.04$, $\eta_g$ is the glass transition temperature viscosity of the heavy oil and a function of $T_{2LM}$, and C1 is a variable which is a constant for the heavy oil and is a function of $T_{2LM}$. Both C1 and $\eta_g$ are considered functions of certain NMR values associated with the heavy oil sample, with $\eta_g$ and C1 preferably estimated by empirically fitting data to the equations ln $T_{2LM}=a'+b'$ ln $\eta_g$ and ln $T_{2LM}=a''+b''C1$, where a', b', a'' and b'' are constants.

9 Claims, 5 Drawing Sheets

METHODS FOR DETERMINING IN SITU THE VISCOSITY OF HEAVY OIL USING NUCLEAR MAGNETIC RESONANCE RELAXATION TIME MEASUREMENTS

BACKGROUND OF THE INVENTION

1. Field of the Invention

The invention relates broadly to the investigation of geological formations. More particularly, this invention relates to in situ methods of determining the viscosity of heavy oils using nuclear magnetic resonance (NMR) techniques.

2. Description of Related Art

Most of the world's oil reservoirs contain heavy and viscous hydrocarbons which are difficult and costly to produce. Heavy oil viscosity is one of the few criteria available to assess production economics by helping predict if cold production will yield economic production rates, or if thermal processes will be required to reduce the oil viscosity to achieve the required production rates. If cold production is selected, viscosity is again used to help determine whether vertical or horizontal wells should be used. Viscosity data are also used to adjust cold production exploitation strategies if the production rates are significantly lower than expected.

The use of NMR techniques has been known to provide a good correlation between viscosity and NMR relaxation time for relatively light oils. However, such techniques fail for highly viscous oils (heavy oils).

More particularly, NMR relaxation time of bulk fluids is sensitive to the viscosity and temperature due to the dependence of rotational and translational correlation times of fluids. Presently in the petroleum industry, there are three widely used correlations between oil viscosity and the NMR logarithmic mean of the spin-spin relaxation time distribution:

$$T_{2LM} = \frac{1200}{\eta^{0.9}} \text{ (Straley-Kleinberg-Vinegar correlation)} \quad (1)$$

$$T_{2LM} = 7.13 \frac{T}{\eta} \text{ (Zega-Zhange correlation)} \quad (2)$$

$$T_{2LM} = 9.56 \frac{T}{\eta} \text{ (Lo correlation)} \quad (3)$$

where $\eta$ is the viscosity of the oil in centipoise (cp), T is the temperature in degrees Kelvin, and $T_{2LM}$ is the logarithmic mean of the $T_2$ distribution in milliseconds (msec). Unfortunately, as can be seen from FIG. 1 which plots the viscosity values measured in a lab (using a capillary viscometer) for heavy oil (HO) samples collected from different locations against the viscosities predicted by the correlations set forth above (using a 2 MHz Maran Ultra NMR instrument available from Oxford Instruments plc of Abingdon, Oxon, United Kingdom), none of the above expressions provided a good correlation.

BRIEF SUMMARY OF THE INVENTION

According to the invention, the viscosity $\eta$ (in centipoise) of a heavy oil sample (i.e., an oil having an API gravity of 22.3 degrees or less) is determined according to an equation of the form $$\ln \frac{\eta}{\eta_g} = \frac{-C1 * (T - c'246)}{c''47.10 + (T - c'246)} \quad (4)$$

where T is the temperature in degrees Kelvin of the heavy oil sample, C1 is a constant associated with the oil sample, c' is a constant between 0.95 and 1.05 (preferably 1.0), c" is a constant between 0.96 and 1.04 (preferably 1.0), and $\eta_g$ is the viscosity of the heavy oil at its glass transition temperature.

According to one aspect of the invention, both C1 and $\eta_g$ are considered functions of certain NMR values associated with the heavy oil sample. More particularly, both C1 and $\eta_g$ are considered functions of the logarithmic mean of the measurable $T_2$ distribution of the heavy oil sample. The glass transition temperature viscosity $\eta_g$ can be estimated by empirically fitting data to the equation $$\ln T_{2LM} = a' + b' \ln \eta_g \quad (5)$$

while C1 can be estimated by empirically fitting data to the equation $$\ln T_{2LM} = a'' + b'' \ln C1 \quad (6)$$

In a preferred embodiment, a'=6.16 and b'=−0.18, while a"=6.34 and b"=−0.16. Depending upon the particular NMR experiment conducted and the equipment utilized, a', b', a", and b" may change somewhat, thereby affecting the determinations of C1 and $\eta_g$. However, the resulting change in the determination of the value of the viscosity $\eta$ will be small.

According to another aspect of the invention, the viscosity of a heavy oil sample is determined in situ in a formation by placing an NMR tool into a borehole in the formation, conducting an NMR experiment on the formation's heavy oil sufficient to generate a $T_2$ distribution, and using the $T_2$ distribution obtained from the experiment, determining the viscosity of the heavy oil sample according to an equation of the form of Equation (4) above.

Objects and advantages of the invention will become apparent to those skilled in the art upon reference to the detailed description taken in conjunction with the provided figures.

DETAILED DESCRIPTION OF THE INVENTION

Figure 1:
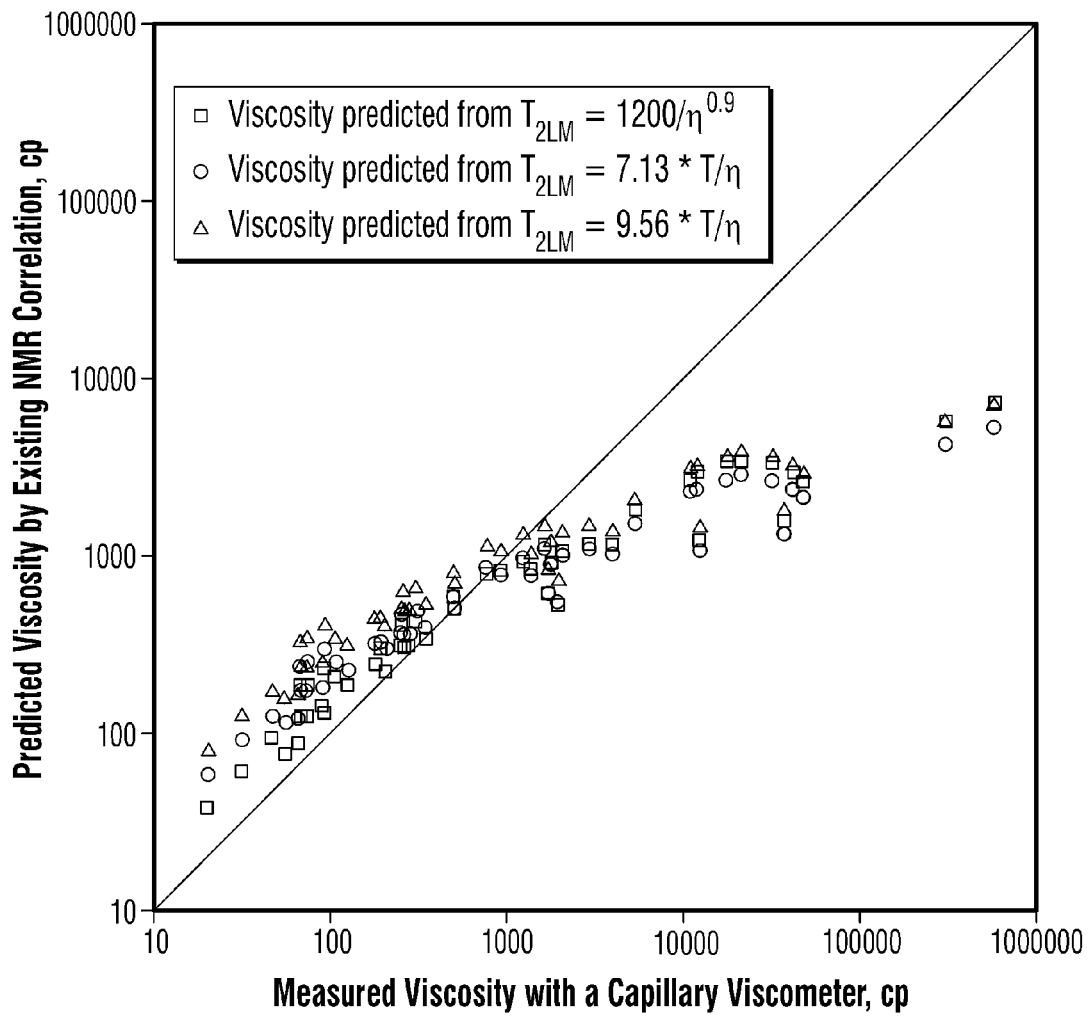
FIG. 1 is a double logarithmic plot showing predicted viscosities of heavy oil samples using prior art correlations versus the measured viscosities.

Before discussing the methods of the invention, a theoretical understanding is useful of how a relationship between viscosity of heavy oil samples and NMR test results can be generated.

A starting point for the theoretical understanding does not relate to heavy oils at all, but rather deals with the relationship of viscosity and temperature of simple liquids. The temperature dependence of the viscosity of a liquid is readily observable as the viscosity of the liquid tends to fall (i.e., its fluidity increases) as the temperature of the liquid increases. In the 1890's, Arrhenius showed that there is a logarithmic relationship between viscosity and inverse temperature in many fluids. While this logarithmic relationship well describes certain liquids, it was found that the Arrhenius equations did not describe polymers, such as plastics, which underwent a "glass transition", a pseudo-second order transition in which melt plastics become rigid on cooling. A model based on free volume theory has been used for polymers. In the free volume model, the molecules are thought to be confined in a space surrounded by their immediate neighbors and perform considerable displacement within it due to an occasional fluctuation in density. The translation of the molecules across the void is a result of activation rather than a result of redistribution of the free volume within the liquid. The free volume of a given molecule is the volume within its surroundings less the volume of the molecule and it should exceed a critical volume just large enough to permit another molecule to jump in after the displacement.

In 1950, Flory and Fox postulated that glass expands at constant free volume, i.e., that glassy expansion, which is much weaker than melt/rubber thermal expansion, involves expansion of the occupied volume of the sample at constant free volume. By inducing the dependence of the free volume $v_f$ on temperature T, the molecular motion results in a viscosity $\eta$ for the polymer which can be described by the William-Landel-Ferry (WLF) equation (Williams, M. et al., *Journal of the American Chemical Society* 77, 3701(1955)):

$$\ln\frac{\eta}{\eta_g} = \frac{-C1*(T-T_g)}{C2+(T-T_g)} \qquad (7)$$

where T is the temperature in degrees Kelvin of the polymer, $T_g$ is the glass transition temperature of the polymer, C1 and C2 are constants for the polymer, and $\eta_g$ is the viscosity of the polymer at its glass transition temperature. According to Doolittle (Doolittle, A. K., *Journal of Applied Physics*, 22, 1471(1951), $C1=v*/v_g$ where $v*$ is the required free volume to perform a jump and $v_g$ is the free volume at the glass transition temperature $T_g$. In addition, $C2=(v_g/v_m)\Delta\alpha$, where $v_m$ is the fictive volume of the molecule at absolute zero without free volume, and $\Delta\alpha$ is the difference of the thermal expansion coefficients in the glassy and the liquid phases, respectively.

Although Equation (7) was obtained empirically to describe the temperature dependence of viscosity of polymer materials, to the best of Applicants' knowledge, it has never been used in conjunction with heavy oils in geological formations. As will be discussed in more detail hereinafter, the Applicants determined that for heavy oils, the values of C2 and $T_g$ do not vary widely and may be assumed to be constant values, whereas the values of C1 and $\eta_g$ do vary and mast be determined. In addition, from the above-discussed physical meanings, it is believed that C1 and $\eta_g$ are related to the flow properties of the substance being tested. From Equation (7), it appears that the larger C1 and $\eta_g$ are, the more viscous the liquid is; i.e., the value for Equation (7) gets larger with a larger C1 and a larger $\eta_g$.

As set forth above, relationships between the NMR $T_2$ spin-spin relaxation time and the viscosity of lighter oils have been posited for some time. In general, the NMR $T_2$ time increases with increasing $\eta_g$ and with decreasing C1. Thus, it is posited that $\eta_g$ and C1 may be estimated from NMR measurements according to linear equations such as Equations (5) and (6) set forth above; i.e., $\ln T_{2LM}=a'+b' \ln \eta_g$ and $\ln T_{2LM}=a''+b'' \ln C1$, where $T_{2LM}$ is the logarithmic mean of the $T_2$ distribution and is given by $$T_{2LM} = \left(\prod_{i=1}^{n} T_{2i}^{n_i}\right)1 / \sum_i n_i, \text{ or } \ln(T_{2LM}) = \frac{\sum_i n_i \ln(T_{2i})}{\sum_i n_i} \qquad (8)$$

where $n_i$ is the mole of proton corresponding to the i-th component with $T_2$ relaxation time in the $T_2$ distribution. Thus, generally, using NMR measurements, in situ determinations of $\eta_g$ and C1 may be estimated using Equations (5) and (6). From those estimations and from Equation (7), an in situ estimation (determination) of the viscosity of the heavy oil sample can be made at any temperature.

Given the above understanding of how the viscosity of heavy oil can be determined from NMR test results, fourteen heavy oil samples were collected from different regions of the world. Their viscosities at different temperatures were measured with a capillary viscometer. Table 1 presents the viscosity data (all numbers in centipoise) of the fourteen heavy oils at eight different temperatures:

TABLE 1

| Samples | 10° C. | 20° C. | 25° C. | 50° C. | 80° C. | 120° C. | 160° C. | 200° C. |
|---|---|---|---|---|---|---|---|---|
| HO#1 | x | 73,000 | 37,400 | 2908 | 372 | 64.5 | 21.4 | 10.0 |
| HO#2 | 249,408 | x | 30,956 | 2111 | 259 | 45.8 | 14.8 | 6.8 |
| HO#4 | 140,151 | x | 17,805 | 1473 | 198 | 37.6 | 12.1 | 5.9 |
| HO#5 | 316,417 | x | 35,978 | 2722 | 356 | 57.0 | 16.8 | 7.9 |
| HO#6 | x | x | 14,816 | 1322 | 193 | 38.6 | 13.1 | 6.4 |
| HO#7 | z | x | 572,472 | 19,272 | 1370 | 145.0 | 32.6 | 13.0 |
| HO#8 | x | x | 5415 | 530 | 82 | 17.2 | 6.2 | 3.0 |
| HO#9 | x | x | 1290 | 194 | 42 | 11.0 | 4.7 | 2.7 |
| HO#10 | x | x | 11,514 | 844 | 109 | 20.7 | 7.0 | 3.6 |
| HO#11 | x | x | 41,051 | 2259 | 222 | 34.2 | 10.4 | 4.8 |
| HO#12 | z | x | 289,067 | 11,886 | 903 | 107.0 | 26.5 | 10.9 |
| HO#13 | x | x | 45,946 | 2827 | 325 | 53.0 | 15.7 | 7.3 |
| HO#14 | z | x | 550,107 | 19,202 | 1358 | 134.0 | 29.5 | 10.9 |
| HO#15 | 21,435 | x | 3810 | 507 | 94.9 | 22.4 | 8.36 | 4.40 | x = not determined.
z = not measurable.

Figure 2:
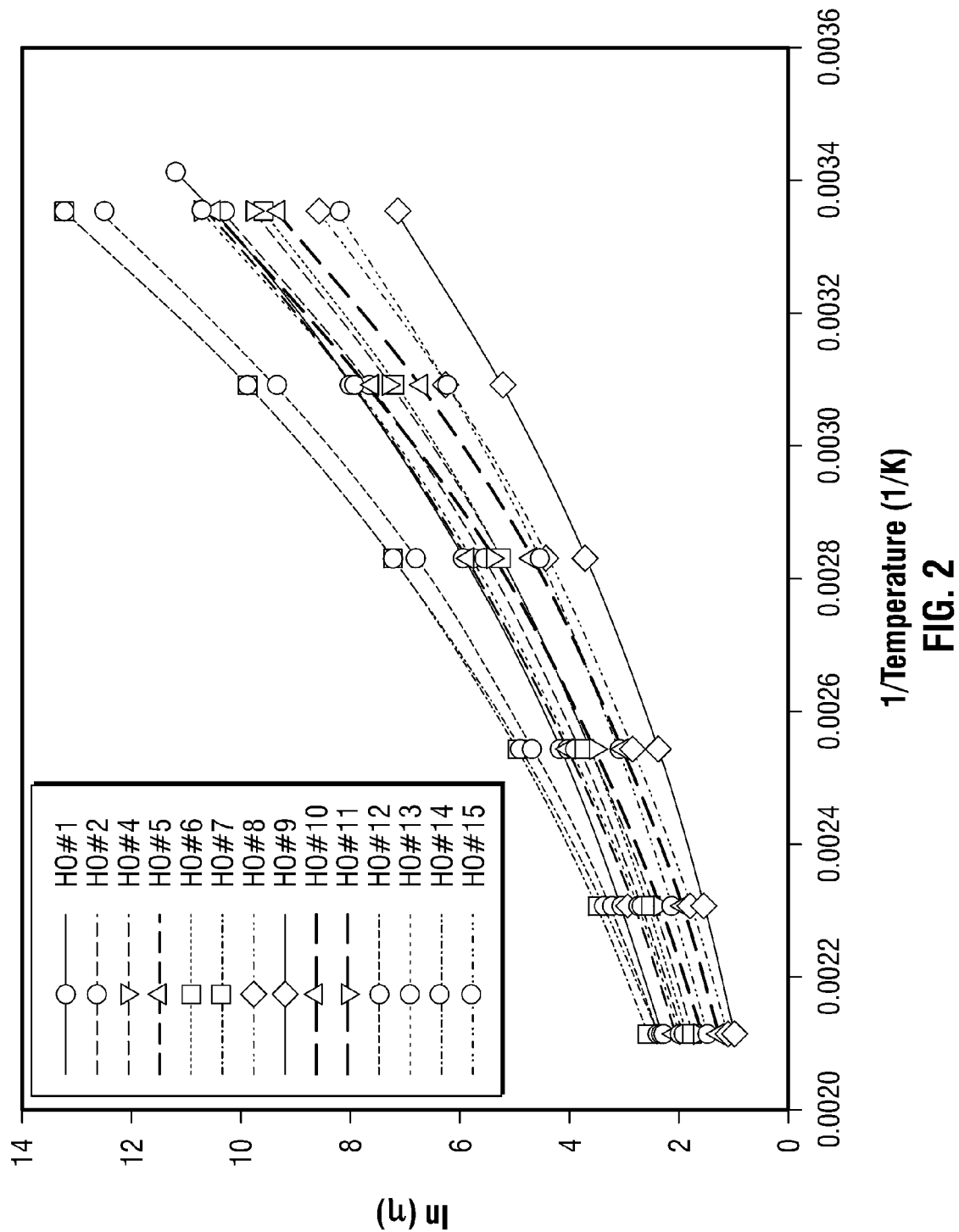
FIG. 2 is a graph showing the relationship between the viscosity and temperature of fourteen different heavy oil samples.

FIG. 2 is a graph showing the relationship between the viscosity and temperature of the fourteen different heavy oil samples. FIG. 2 graphs the natural log of the viscosity (taken from the data set of Table 1) of the heavy oil samples against the inverse of the Kelvin temperature at which the viscosity data was obtained.

The viscosity data at different temperatures set forth in Table 1 were fitted to Equation (7) in order to find the glass transition temperature $T_g$, viscosity at the glass transition temperature $\eta_g$, and C1 and C2 by a least squares fitting technique. As a result, as seen in Table 2, the following parameters were obtained for the samples:

TABLE 2

| HO Sample | $T_g$(°K) | ln($\eta_g$) | C1 | C2 |
| --- | --- | --- | --- | --- |
| 1 | 244 | 25.85 | 28.30 | 45.85 |
| 2 | 252 | 22.71 | 25.39 | 48.59 |
| 4 | 246 | 23.70 | 26.54 | 47.38 |
| 5 | 241 | 26.46 | 29.56 | 48.73 |
| 6 | 246 | 23.00 | 25.59 | 47.51 |
| 7 | 249 | 30.63 | 34.05 | 47.26 |
| 8 | 245 | 21.90 | 25.12 | 47.30 |
| 9 | 242 | 19.30 | 21.95 | 45.53 |
| 10 | 254 | 21.06 | 24.05 | 46.65 |
| 11 | 253 | 24.27 | 27.49 | 45.97 |
| 12 | 247 | 30.49 | 33.82 | 45.52 |
| 13 | 251 | 23.89 | 26.75 | 48.76 |
| 14 | 244 | 32.65 | 36.66 | 48.06 |
| 15 | 235 | 23.35 | 26.15 | 46.23 |
| Average | 246 | 24.95 | 27.96 | 47.10 |

From Table 2 it will be appreciated that the values of C2 and $T_g$ do not vary widely across the various heavy oil samples. More particularly, it is seen that for the fourteen samples, C2 varies from a low value of 45.52 to a high value of 48.76, with the average being 47.10, and thus the variation (high or low) from the average is typically 4% or less. Thus, it is reasonable to take C2 as a constant. The constant C2 is preferably set equal to 47.10±4%, and more preferably set equal to 47.10. Similarly, it is seen that for the fourteen samples, the glass transition temperature $T_g$ (°K) varies from a low value of 235 to a high value of 254, with the average being 246, and thus the variation (high or low) from the average it typically 5% or less. Thus, it is reasonable to take $T_g$ as a constant. The constant $T_g$ is preferably set equal to 246±5%, and more preferably set equal to 246.

Figure 3:
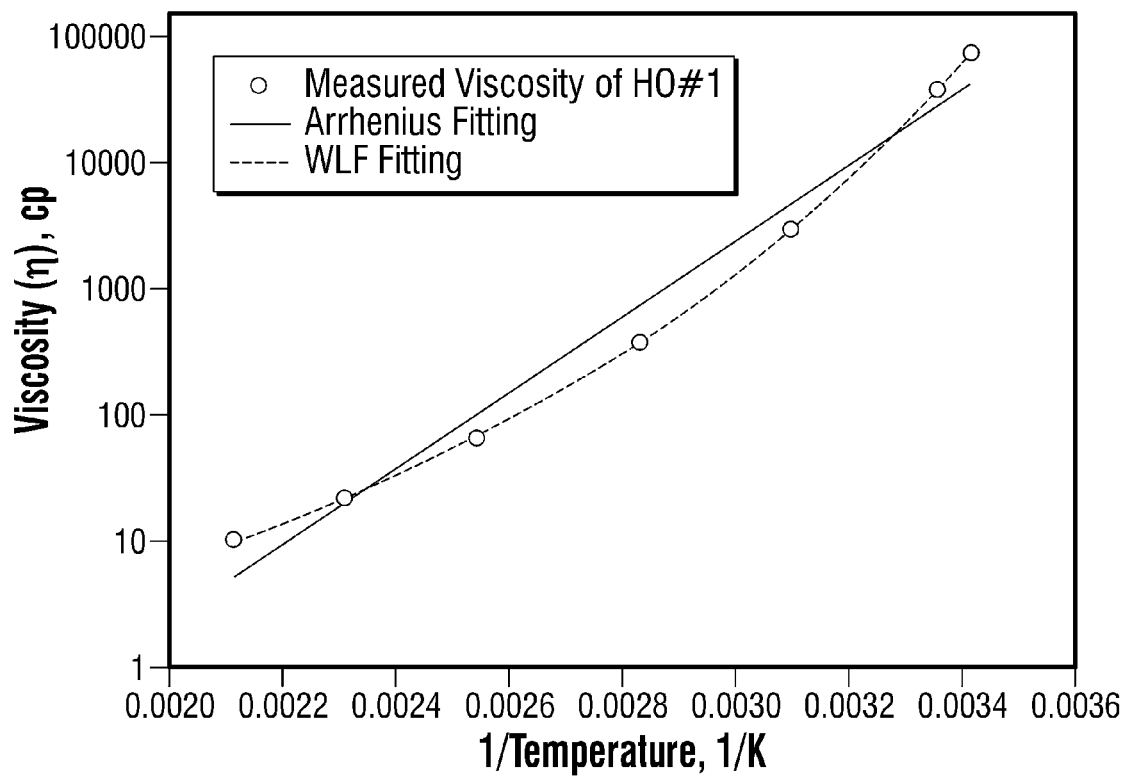
FIG. 3 is a logarithmic plot showing the viscosity of a heavy oil sample as a function of the inverse of its temperature and two different curves fit to the data.

With $T_g$ and C2 set as constants, it will be appreciated that Equation (7) can be rewritten as $$\ln \frac{\eta}{\eta_g} = \frac{-C1*(T-c'246)}{c''47.10+(T-c'246)} \qquad (9)$$

where c' is a constant between 0.95 and 1.05 (i.e., 1.0±5%) and preferably 1.0, and c" is a constant between 0.96 and 1.04 (i.e., 1.0±4%) and preferably equal to 1.0. Equation (9), with c'=1.0 and c"=1.0 was employed to predict the viscosities of heavy oil sample #1 at different temperatures. The predicted viscosities are compared to the measured viscosities in FIG. 3 (which also shows the straight line prediction of the Arrhenius equation) and provides an excellent fit.

While C2 and $T_g$ may be taken as constants, it will be appreciated from Table 2 that the variations in ln($\eta_g$) and C1 (which each range from about 20% to 30%) are much greater, and that neither should be considered a constant for heavy oil. In order to be able to find in situ values for the variables ln($\eta_g$) and C1, relationships were developed between the variables and NMR values that can be determined downhole. To establish the relationships, each of the fourteen heavy oil samples was pressed into temperature controlled ceramic tubes for nuclear magnetic resonance testing. NMR experiments were conducted at a Larmor frequency of 2 MHz on a Maran Ultra NMR instrument. Proton spin-lattice relaxation time ($T_1$) was measured at 10, 15, 25, 50, 80 and 110° C. by the saturation recovery technique. Proton spin-spin relaxation times ($T_2$) were determined at the above-stated temperatures, and a modified Carr-Purcell-Gill-Meiboom (CPGM) sequence ($\pi/2$-$\tau$-$\pi$-$\tau$-echoes-$5T_1$-$\pi/2$-$\tau$-$\pi$-$\tau$-echoes-$5T_1$) was used with $\tau$=100 μs and a cycle time greater than 5 times $T_1$. The $T_2$ distribution was recovered by the inverse Laplace transform of time domain CPGM echo signals. The logarithmic mean of the $T_2$ distribution ($T_{2LM}$) was determined according to Equation (8) above.

Figure 4:
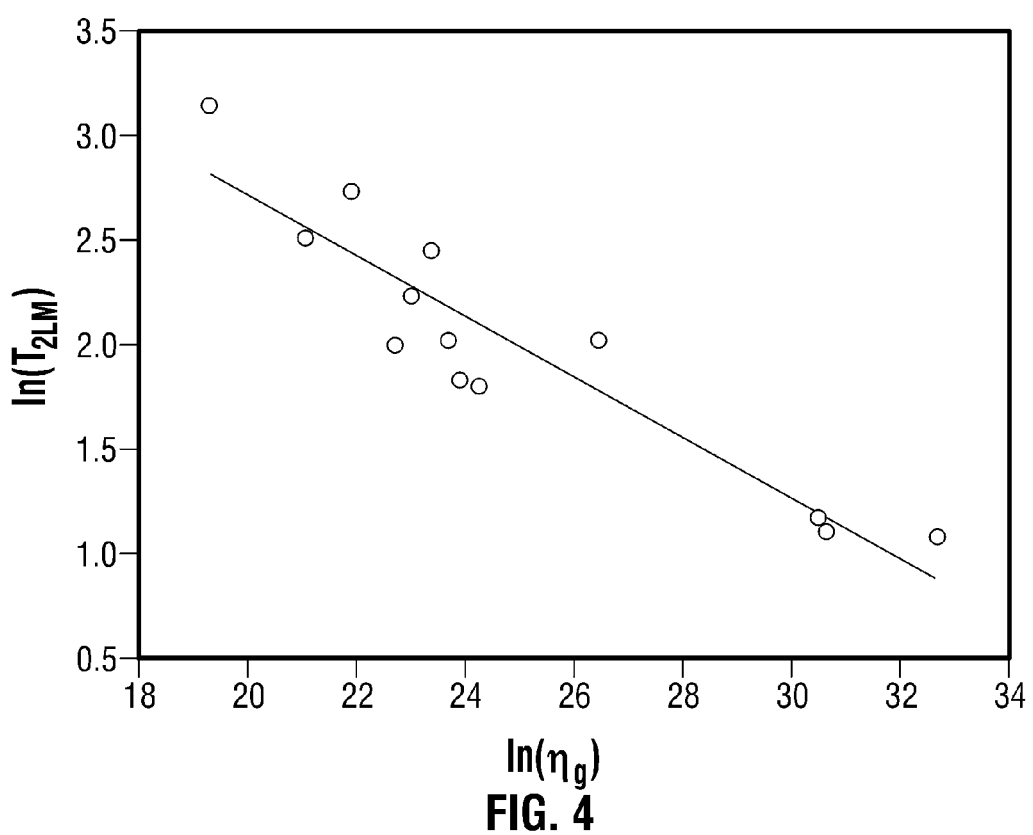
FIG. 4 is a plot showing the correlation of the natural log of $T_{2LM}$ at 80° C. and the natural log of the viscosity of thirteen heavy oil samples at their glass transition temperatures.
Figure 5:
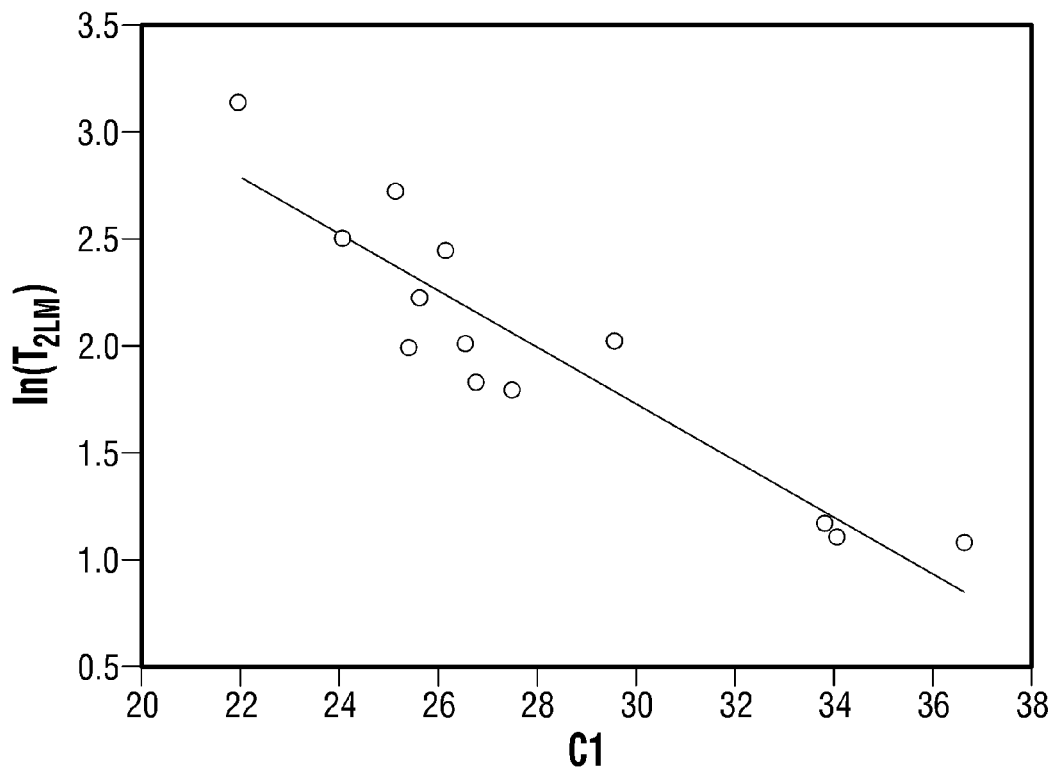
FIG. 5 is a plot showing the correlation of the natural log of $T_{2LM}$ at 80° C. and the constant C1 for thirteen heavy oil samples.

With the $T_{2LM}$ determinations as well as the values for ln($\eta_g$) and C1 established for the heavy oil samples, thirteen of the samples (excluding heavy oil sample #1) were evaluated to obtain the empirical determinations for the constants in Equations (5) and (6): ln $T_{2LM}$=a'+b' ln $\eta_g$; and ln $T_{2LM}$=a"+b"C1. A best fit yielded values of a'=6.16, b'=−0.18, a"=6.34 and b"=−0.16. The correlation between $T_{2LM}$ and ln($\eta_g$) is seen in FIG. 4 ($R^2$=0.84), while the correlation between $T_{2LM}$ and C1 is seen in FIG. 5 ($R^2$=0.81). It will be appreciated that depending upon the particular NMR experiment conducted and the equipment utilized, a', b', a", and b" may change somewhat, thereby affecting the determinations of C1 and $\eta_g$. However, the resulting change in the determination of the value of the viscosity $\eta$ will be small. The viscosity of heavy oil sample #1 was then predicted from Equations (5), (6), and (9) ("leave-one-out" method).

Figure 6:
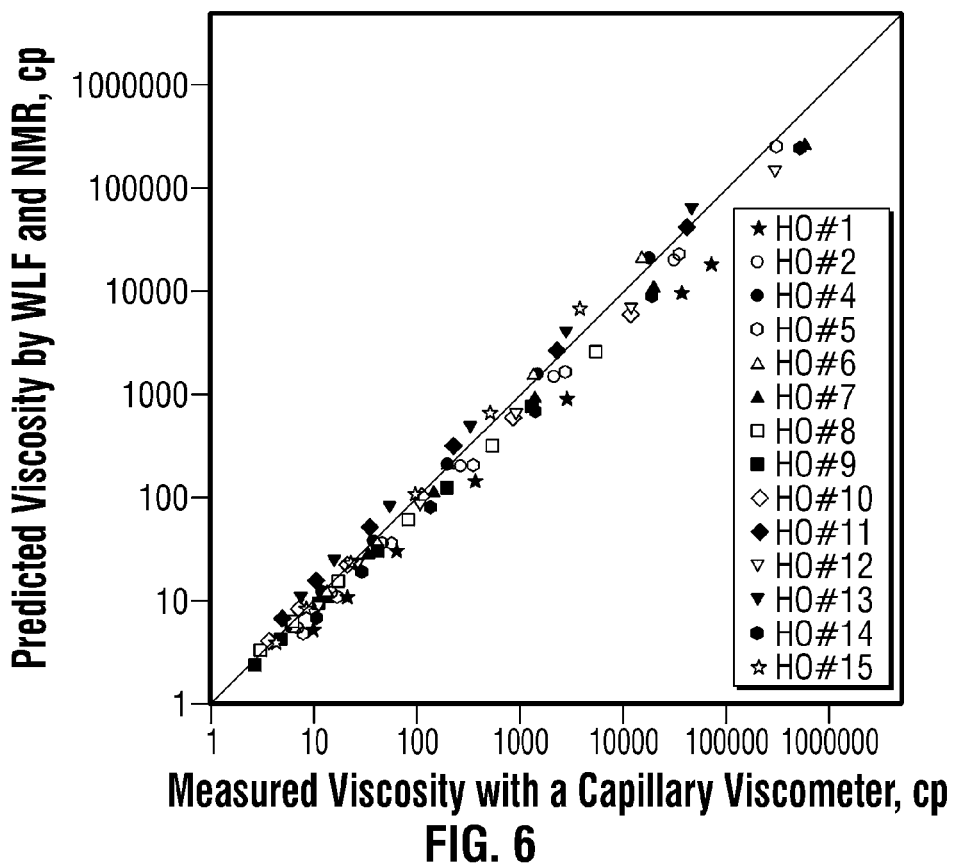
FIG. 6 is a double logarithmic plot comparing measured viscosities of heavy oil samples at different temperatures and the predicted viscosities according to the invention.

The results in FIG. 6 were obtained using the above-referenced "leave-one-out" method whereby each sample was removed from the database of fourteen heavy oil samples and its viscosity was predicted from the remaining thirteen heavy oil samples in the database according to Equations (5), (6), and (9). The predicted viscosities of fourteen of the heavy oil samples at various temperatures were plotted in a logarithmic-logarithmic plot against the measured viscosity of the heavy oil samples. As seen in FIG. 6, the predicted viscosities matched well with the measured viscosities.

Figure 7:
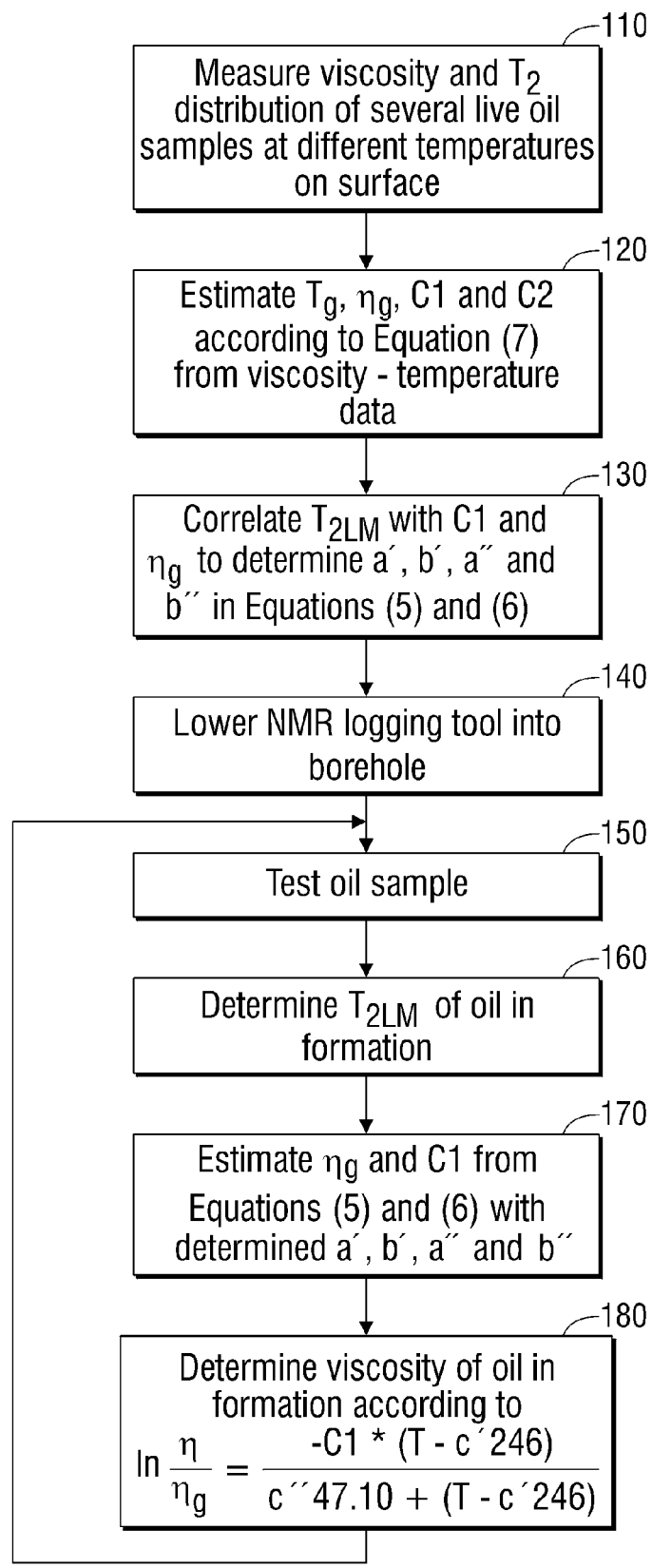
FIG. 7 is a flow diagram of the method of one aspect of the invention.

Turning now to FIG. 7, a flow diagram of a method in accordance with an aspect of the invention is shown. As shown in FIG. 7, at step 110 the viscosity $T_2$ distribution of several live oil samples are measured at different temperatures at the surface. Next, at step 120, the glass transition temperature $T_g$, viscosity at the glass transition temperature $\eta_g$, and constants C1 and C2 are estimated according to Equation (7). At step 130 the logarithmic mean of the $T_2$ distribution, $T_{2LM}$, is correlated with $\eta_g$ and C1 to determine constants a', b', a" and b" in Equations (5) and (6). At step 140 NMR logging tool is lowered in a borehole traversing an earth formation. The logging tool may be any tool capable of making $T_2$ measurements of oil in the formation such as the CMR-Plus tool available from Schlumberger Technology Corporation of Sugar Land, Tex., USA. At step 150, an oil sample at a location in the formation is subjected to testing by the NMR logging tool. At step 160, using the results of the testing, a determination of a $T_{2LM}$ value is made for that sample. Then, at step 170, using the $T_{2LM}$ value and Equations (5) and (6), estimated values for the glass transition temperature viscosity $\eta_g$ and C1 are obtained. Preferably, at step 170, values of a'=6.16, b'=−0.18, a"=6.34 and b"=−0.16 are utilized. However, it will be appreciated that other values could be used. Regardless, at step 180, a determination (estimation) of the viscosity of the in situ oil sample is made using the estimated values for the glass transition temperature viscosity $\eta_g$ and C1, the temperature of the oil sample, and an equation of the form of Equation (9). Steps 150, 160, 170, and 180 may be repeated for any number of oil samples in the formation. The method of FIG. 7 is particularly useful for determining in situ the viscosity of heavy oils in a formation.

Several embodiments of a method of determining in situ the viscosity of heavy oils have been described and illustrated herein. While particular embodiments of the invention have been described, it is not intended that the invention be limited thereto, as it is intended that the invention be as broad in scope as the art will allow and that the specification be read likewise. Thus, while it was disclosed that a particular number (fourteen) of oil samples were used to generate values for certain constants used in finding parameters $\eta_g$ and C1, it will be appreciated that other numbers of samples could be utilized. Also, while a particular NMR tool was described for carrying out the methods, it will be understood that other tools could be used, provided the tool is capable of generating a determination of the $T_2$ distribution. Similarly, while a particular NMR sequence (modified CPGM) was described as being utilized in conjunction with correlating the glass temperature viscosity and the constant C1 to NMR measurements in order to find particular values for a', b', a", and b", it will be appreciated that other sequences could be utilized which would result in other values being utilized. It will therefore be appreciated by those skilled in the art that yet other modifications could be made to the provided invention without deviating from its scope as claimed.

What is claimed is:

1. A method for determining the viscosity of a heavy oil located in a formation traversed by a borehole, comprising:
    a) locating a nuclear magnetic resonance (NMR) logging tool in the borehole;
    b) making $T_2$ measurements of the heavy oil in situ; and
    c) without bringing said heavy oil uphole, determining the viscosity $\eta$ of the heavy oil according to $$\ln\frac{\eta}{\eta_g} = \frac{-C1*(T - c'246)}{c''47.10 + (T - c'246)},$$

where T is the temperature of the heavy oil, $T_{2LM}$ is the logarithmic mean of the $T_2$ distribution of the heavy oil obtainable from said $T_2$ measurements, c' is a constant between 0.95 and 1.05, c" is a constant between 0.96 and 1.04, $\eta_g$ is the glass transition temperature viscosity of the heavy oil and a function of $T_{2LM}$, and C1 is a variable which is a constant for the heavy oil and is a function of $T_{2LM}$.

2. A method according to claim 1, wherein c' has a value of 1.0 and c" has a value of 1.0.

3. A method according to claim 2, further comprising determining $\eta_g$ according to $\ln T_{2LM} = a' + b'' \ln \eta_g$, where a' and b' are constants.

4. A method according to claim 3, further comprising determining C1 according to $\ln T_{2LM} = a'' + b'' \ln C1$, where a" and b" are constants.

5. A method according to claim 4, further comprising finding a', b', a" and b" empirically by testing a plurality of heavy oil samples.

6. A method according to claim 4, wherein a'=6.16, b'=−0.18, a"=6.34 and b" −0.16.

7. A method according to claim 1, further comprising:
    prior to locating said NMR logging tool in the borehole, obtaining a plurality of samples of heavy oil from at least one formation;
    testing said plurality of samples of heavy oil to obtain glass transition temperatures of said heavy oil samples; and
    averaging said glass transition temperatures to obtain an average, wherein c'246 equals said average.

8. A method according to claim 7, further comprising:
    testing said plurality of samples of heavy oil to obtain a glass transition viscosity value for each heavy oil sample at its glass transition temperature;
    measuring viscosity values for each sample of heavy oil at a plurality of different temperatures; and
    using said viscosity values at different temperatures and said glass transition viscosity values, and said glass transition temperatures, finding values for a variable C2;
    averaging said C2 values to find a C2 average, wherein c"47.10 equals said C2 average.

9. A method according to claim 1, further comprising moving said NMR logging tool in the borehole, wherein making $T_2$ measurements of the heavy oil in situ comprises making $T_2$ measurements of multiple samples of heavy oil, and determining the viscosity $\eta$ of the heavy oil comprises determining the viscosities of the multiple samples of heavy oil.

* * * * *